United States Patent [19]

Saba et al.

[11] Patent Number: 5,082,934
[45] Date of Patent: Jan. 21, 1992

[54] COUMARIN DERIVATIVES FOR USE AS NUCLEOTIDE CROSSLINKING REAGENTS

[75] Inventors: Don Saba; Richard S. Glass, both of Tucson, Ariz.; Kenichi K. Yabusaki, Albany, Calif.

[73] Assignee: Naxcor, Albany, Calif.

[21] Appl. No.: 333,632

[22] Filed: Apr. 5, 1989

[51] Int. Cl.$^5$ .......................................... C07H 19/067
[52] U.S. Cl. .................... 536/17.6; 536/17.2; 536/17.9; 536/18.1; 536/22; 536/27
[58] Field of Search ............ 536/22, 23, 8.8, 17.2, 536/17.9, 18.1, 29, 26, 27, 28, 17.6

[56] References Cited

U.S. PATENT DOCUMENTS 4,826,967 5/1989 Glass ................................ 536/22

*Primary Examiner*—Johnnie R. Brown
*Assistant Examiner*—Elli Peselev
*Attorney, Agent, or Firm*—Cooley Godward Castro Huddleson & Tatum

[57] ABSTRACT

A photoactivatible nucleoside analogue is disclosed, comprising a coumarin moiety linked through its phenyl ring to the 1-position of a ribose or deoxyribose sugar moiety. The resulting nucleoside analogue is typically used as a photocrosslinking group when inserted into a polynucleotide as a replacement for one or more of the complementary nucleoside bases present in a probe used in a hybridization assay.

10 Claims, No Drawings

COUMARIN DERIVATIVES FOR USE AS NUCLEOTIDE CROSSLINKING REAGENTS

TECHNICAL FIELD

This invention relates to photoreactive nucleotide analogues that can be used to crosslink complementary nucleic acid sequences.

BACKGROUND

There is considerable interest in developing techniques for determining the presence of analytes of biological origin in samples, particularly clinical samples. One technique uses the complementary binding known as hybridization that takes place between complementary strands of nucleic acids such as DNA and RNA to identify the presence of analytes containing DNA or RNA in samples.

Specific hybridization techniques have been developed for determining the presence of a specific virus, bacterium, or other organism in a biological sample, as well as for detecting genetic defects in mammalian cells. Among the recently developed techniques are those that rely on the formation of a covalent bond between the target and the reagent polynucleotide strands. In one such technique, a nucleic acid reagent (probe) is created containing a covalently linked, photoactivatable moiety that is capable of forming covalent bonds with the analyte upon photoactivation. If a probe and analyte are mixed under hybridizing conditions and the linking group is photoactivated, covalent bonds are formed that bind the two strands together. If the probe also contains a detectable signal, rigorous techniques for separating single and double-stranded nucleic acids can be utilized to determine the presence of analyte in the sample by determining the presence of crosslinked nucleic acid strands. For example, U.S. Pat. No. 4,599,303 to Yabusaki et al. describes nucleic acid hybridization techniques that employ probes that are crosslinkable to target sequences.

These prior techniques have typically relied on the use of a photoactivatible group that is covalently attached to a base residue of a polynucleotide. However, synthesis of the known photoactivatible probes is difficult, particularly in large scale.

Accordingly, new techniques that rely on more readily available analogues of nucleotides that are photoactivatible are desirable.

SUMMARY OF THE INVENTION

The present invention provides photoactivatible compounds that can be used as photocrosslinkable reagents in hybridization assays as well as techniques and intermediates that can be used to prepare the final products. The compounds comprise nucleoside analogues prepared by linking the phenyl ring (especially at the 7 position) of a coumarin or coumarin analogue to the 1 position of a D-ribose or D-2-deoxyribose molecule. The double bond between the 3 and 4 positions of the coumarin ring system is the photoactivatible group that covalently crosslinks to nucleosides in the complementary strand when a probe containing this nucleoside analogue is used in a hybridization assay. For the most part, the photoactivatible compound has the formula

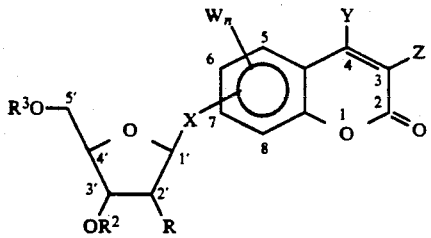

in which the substituents and linking groups are described below in more detail.

DESCRIPTION OF SPECIFIC EMBODIMENTS

The present invention arose in part from investigations into the use of various coumarin derivatives to act as divalent photoactivatible crosslinking groups in hybridization assays. In particular, one double bond of a psoralen was reacted with a nucleoside to produce an adduct that retained (typically, after removal of a blocking group) a photoactivatable double bond. When this adduct is incorporated into an oligonucleotide and hybridized with a complementary oligonucleotide, crosslinking occurs upon photoactivation. Such molecules are described in copending application Ser. No. 07/063,23 now U.S. Pat. No. 4,826,967. Although this type of crosslinking group is satisfactory for many applications, the crosslinking-group/nucleoside adduct is difficult to synthesize, particularly in large quantities.

In the course of investigating smaller crosslinkable groups, the present inventors determined that the nucleoside base can be eliminated entirely without adversely affecting hybridization in the adjacent region. The nucleoside analogue of the invention comprises a photoactivatible coumarin attached to a sugar in the position that the base normally occupies. By providing a relatively small photoactivatible group, hybridization occurs efficiently even though the base that would normally participate in recognition between nucleic acid strands is now missing. The coumarin moiety intercalates with the complementary oligonucleotide strand during hybridization and is thereby properly positioned for photocrosslinking to a thymine residue on the complementary strand Additionally, large quantities of crosslinkable probes can be prepared more easily than was possible by prior art techniques that used photoactivation to form an adduct between a psoralen and a nucleoside base.

The particular photoactivatible compounds of the invention are prepared by linking the phenyl ring (preferably at the 7-position) of a coumarin moiety to the 1-position of a D-ribose or D-2-ribose moiety. The coumarin moiety will minimally contain the central 1,2-benzopyrone structure of coumarin which may be unsubstituted (except for the obligatory link to the sugar moiety) or substituted. When a substituent is present on the phenyl ring or at the 3 or 4 position of the coumarin moiety, typically from 1 to 3 stable organic substituents of the types normally found on aromatic rings and as vinyl substituent are present, although more substituents (up to the maximum possible) can be present if the substituents are selected to avoid steric hindrance and are otherwise selected to be compatible according to standards of organic chemistry. These substituents are generally small, containing up to 15 total atoms (including hydrogens). Such substituents are generally selected from halogen, nitro, cyano, carbonyl, carboxy, hydroxy, amino, and amido groups; hydrocarbyl groups substituted by one or more of said groups; and unsubstituted hydrocarbyl groups. The substituents at the 3 and 4 positions of the coumarin moiety are typically lower hydrocarbyl groups, generally lower alkyl groups.

Compounds of the invention preferably have the formula

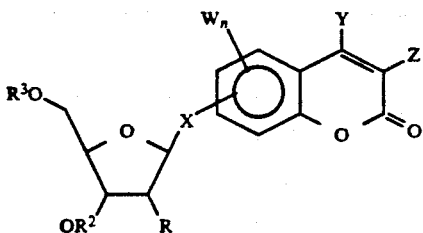

wherein n is 0, 1, 2, or 3 (preferably 0, 1, 2; more preferably 0 or 1); each W is independently a small, stable substituent containing up to 15 atoms (especially a lower hydrocarbyl group; a halogen, nitro, cyano, carbonyl, carboxy, hydroxy, amino, or amido group; or a hydrocarbyl substituent containing one or more of said groups comprising hetero atoms); Y and Z independently represent H or a lower alkyl group; X is an organic linking group containing (a) 1 to 5 carbon atoms, (b) 0 to 3 hetero atoms selected from the group consisting of O, S, and N, (c) and 0 to 2m halogen atoms (where m is the number of carbon atoms in X; halogens α to heteroatoms, such as

are not permitted because of problems relating to stability) and wherein X comprises a linking chain of 1 to 4 atoms; R is H or $OR^1$; and $R^1$, $R^2$, and $R^3$ independently represent H or group capable of coupling with or protecting a hydroxyl group during automated polynucleotide synthesis, or $R^2$ or $R^3$ represents a nucleotide or polynucleotide linked to said compound by a 3'-5' phosphodiester linkage. Preferred coupling groups include phosphorus containing linking groups, such as phosphites, phosphoramidites, phosphates, H-phosphonates, phosphorothioates, and methylphosphonates. Other non-phosphorus coupling groups include carbamates and amides. Lower hydrocarbyl groups include $C_1$–$C_6$ alkyl groups, both linear and branched (and $C_2$–$C_6$ alkenyl and alkynyl groups as well as $C_3$–$C_6$ cyclic groups), and preferably include $C_1$–$C_4$ alkyl groups, especially methyl, ethyl, propyl, isopropyl, butyl, isobutyl, s-butyl, and t-butyl. Typical hydrocarbyl groups with hetero atom substituents include —COCH$_3$, —CH$_2$OH, —CF$_3$, —NHCH$_3$, —CO$_2$CH$_2$CH$_3$, and —CON(CH$_3$)$_2$. The sterochemistry of the ribose or 2-deoxyribose sugar moiety is the same as that present in natural nucleotides (i.e., they are D sugars). Any reference herein to a sugar moiety implies a D sugar unless otherwise specified.

Compounds of the invention are usable either as intermediates in the preparation of, or as components of, photoactivatible polynucleotides used as reagents (typically known as "probes") in hybridization assays. Since the intention is that these molecules eventually form part of a polynucleotide, the sugar moiety that forms part of the molecule is derived either from a ribose or a deoxyribose molecule. The ribose or deoxyribose molecule is incorporated in a polymeric sugar backbone in which the individual sugar groups are linked by phosphodiester groups between 3' and 5' hydroxyl groups. The numbering system used herein is the same as that used in nucleotides, in which the atoms of the "base'- '—here the coumarin derivative—are identified by arabic numbers and the positions of atoms in the sugar moiety are identified by primed arabic numbers.

The coumarin portion of the compound of the invention can be derived from coumarin itself or any of a number of substituted coumarins. A group at the position where the sugar will be attached (referred to in this specification as the linking position) typically functions as a precursor of the linking group that will join the coumarin moiety to the sugar moiety in the final product. However, since final products can be often prepared by alternative synthetic routes, any given final product will likely have several possible precursors. Additionally, it is possible that only a portion of the linking group is prepared from the substituent at the linking position of the coumarin, with the remaining portion of the linking group being derived from the sugar moiety. In fact, this is typically the case when the hydroxy group at the 1' position of the sugar, or a different reactive substituent at this position such as an amino or thio group, is reacted with a leaving group on the substituent in order to form a covalent bond.

At locations other than the linking position, the coumarin ring system can be either unsubstituted or substituted. Typical substituents on the phenyl ring are small substuents normally found on aromatic rings in organic compounds. Substituents can be selected as desired to change the excitation wavelength of the coumarin. Substituents at the 3 and 4 positions are typically non-polar and are most often hydrocarbon substituents, with methyl substituents being most common. Although locations of substituents can vary, substituents are most often found at the 4- and 8-positions.

In certain preferred embodiments the coumarin moiety prior to reaction with the sugar moiety typically has the formula

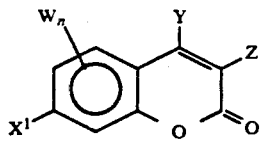

in which Y, Z, n, and W have the meanings previously defined and $X^1$ is a precursor of all or part of the X linking group. Since $X^1$ will react with an organic functional group on the sugar moiety to form a covalent bond in the final linking X group, a reactive functional group must be present in $X^1$. Typical reactive functional groups are nucleophilic and electrophilic groups that are capable of undergoing nucleophilic or electrophilic substitution or addition reactions. The functional group may be one that is fully or partially retained in the final product (such as a hydroxyl group that participates in an $S_N2$ reaction with a leaving group on the sugar moiety) or a leaving group that is not present in the final product (such as a halogen that participates in an $S_N1$ reaction or an $S_N2$ reaction with a hydroxyl on the sugar moiety). Examples of specific functional groups include hydroxy, amino, halogen, thiol, carbonyl, and carboxy (including ester and amide) groups. These precursors can be synthesized by standard methods of organic synthesis from coumarin itself or from the many commercially available coumarin derivatives. See, for example, page 452 of the 1988 Sigma Chemical Co. Catalogue of Biochemical and Organic Compounds and pages 406 and 407 of the 1988-1989 Aldrich Catalog Handbook of Fine Chemicals.

The remainder of the $X^1$ precursor is not particularly limited as long as the previously noted restrictions on size and polarity are present, namely that the final X group is non-polar to moderately polar (typically not containing free hydroxyl or amino groups of the groups previously mentioned) and containing 1 to 5 carbon atoms and 0 to 3 hetero atoms selected from the group consisting of O, S, and N, and wherein the final X group comprises a linking chain of 1 to 4 atoms between the 1' position of the sugar and the linking position of the coumarin derivative. Halogens may also be present, typically in halogenated hydrocarbon bridging groups (up to 2m halogens, where m is the number of carbon atoms in the bridging group). Preferably, the X linking group has the formula $X^2$, $OX^2$, $SX^2$, or $NHX^2$ in which $X^2$ is a $C_1$-$C_5$ hydrocarbyl group or a $C_1$-$C_5$ hydrocarboxy group either of which is substituted with 0 to 2 carbonyl oxygens in the form of keto or ester functionalities (or similar), with the provisos that when O, S, or NH is present as part of X, the O, S or NH (or one such group if more than one is present) is attached to the 1' position of the sugar ring and the $X^2$ group attaches to the indicated hetero atom to form a stable covalent bond. Particularly preferred linking groups are those in which X is $$-OCH_2-, -SCH_2-, -NHCH_2-, -\overset{O}{\underset{\|}{O}C}-, -\overset{O}{\underset{\|}{S}C}-,$$

$$-\overset{O}{\underset{\|}{N}HC}-, -\overset{O}{\underset{\|}{O}CCH_2O}-, -\overset{O}{\underset{\|}{S}CCH_2O}- -\overset{O}{\underset{\|}{O}CCH_2S}-, \text{ or}$$

$$-X^3-(CH_2)_m-$$

where m is an integer from 2 to 4 and $X^3$ is O, S, or NH.

Especially preferred linking groups have 2 atoms in the linking chain, such as the first 6 groups of the preceeding sentence.

The indicated groups on the sugar moiety in the general formula, namely the R, $R^2$ and $R^3$ groups, are those typically present on the sugar moiety of a nucleotide, polynucleotide, or precursor in the synthesis of a polynucleotide by synthetic chemical means, particularly protecting groups and activating groups that are present in solid-phase synthesis. R is either H or $OR^1$, in which $R^1$ is defined below. When R is H, the sugar is deoxyribose, and the nucleoside analogue is intended to be incorporated into a DNA molecule. When R is $OR^1$, the sugar is ribose or a ribose-derivative, and the nucleoside analogue is intended to be incorporated into an RNA molecule.

$R^1$, $R^2$, and $R^3$ independently represent H or a hydroxyl-protecting or a hydroxyl-coupling group and $R^2$ and $R^3$ further can comprise a nucleotide or polynucleotide linked to the remainder of the molecule, typically by a 3'-5' phosphodiester linkage. More particularly, hydroxyl-protecting and hydroxyl-coupling groups are those normally used in nucleotide chemistry, especially in solid-phase chemical synthesis of DNA and RNA molecules in which a chemical linkage through a 3' or 5' hydroxyl group with a nucleoside, nucleoside derivative, polynucleotide, or polynucleotide is a goal of the synthetic process. For a review of such chemistry and the types of protecting and coupling groups that are typically present on sugar moieties during synthesis of a polynucleotide, see "Oligonucleotide Synthesis, a Practical Approach," M. J. Gait, ed., IRL Press Ltd., Oxford, Great Britain 1984; Reese, G. B., *Tetrahedron* (1978) 34:3143; and Amarnath, V. and A. D. Broom, *Chemical Reviews* (1977) 77:183. Particularly preferred are compounds in which $R^1$, $R^2$ and $R^3$ are independently selected from H; benzoyl; benzoyl substituted with $C_1$-$C_4$ alkyl, $C_1$-$C_4$ alkoxy, cyano, nitro, or halogen; triarylmethyl (in which aryl is usually selected from phenyl and naphthyl); or triarylmethyl substituted with $C_1$-$C_4$ alkyl, $C_1$-$C_4$ alkoxyl, cyano, nitro or other small organic groups. The trityl and substituted trityl (especially 4, 4'-dimethoxytrityl) substituents are particularly preferred for $R^3$, as these groups are often used in solid-phase synthesis at this position. A pixyl (9-phenylxanthenyl) group is also commonly used. Trityl and substituted trityl groups are less commonly used as $R^1$ and $R^2$. The 4-methoxytetrahydropyran-4-yl group is preferred for $R^1$.

Compounds of the invention can be prepared by standard techniques of synthetic organic chemistry, using the guidelines as set forth in this specification. For example, a typical synthesis based on commercially available starting materials is set forth in the following reaction scheme. Abbreviations used in the scheme are as follows: NBS=N-bromosuccinimide; DME=1,2-dimethoxyethane; pyr=pyridine; DMT-Cl=dimethoxytrityl chloride; (iPr)$_2$EtN=diisopropylethylamine. Additional details for the reactions shown are set forth in the Examples that follow. Only one of the two possible anomers at the 1-positions of the sugar is shown. Mixtures of α- and β-anomers are usually obtained in synthesis. Separation of anomers to provide pure single anomers can be accomplished at various stages of the synthesis, as shown in the following Examples (e.g., Example 6).

Reaction Scheme

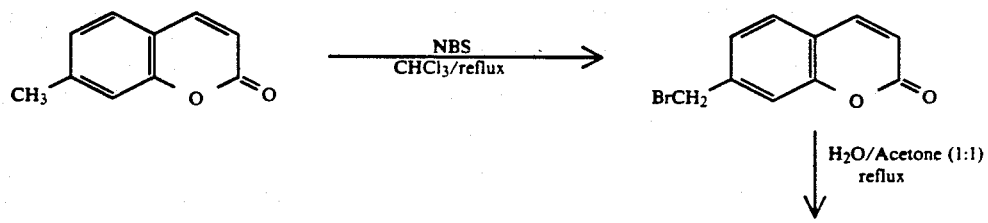

-continued
Reaction Scheme

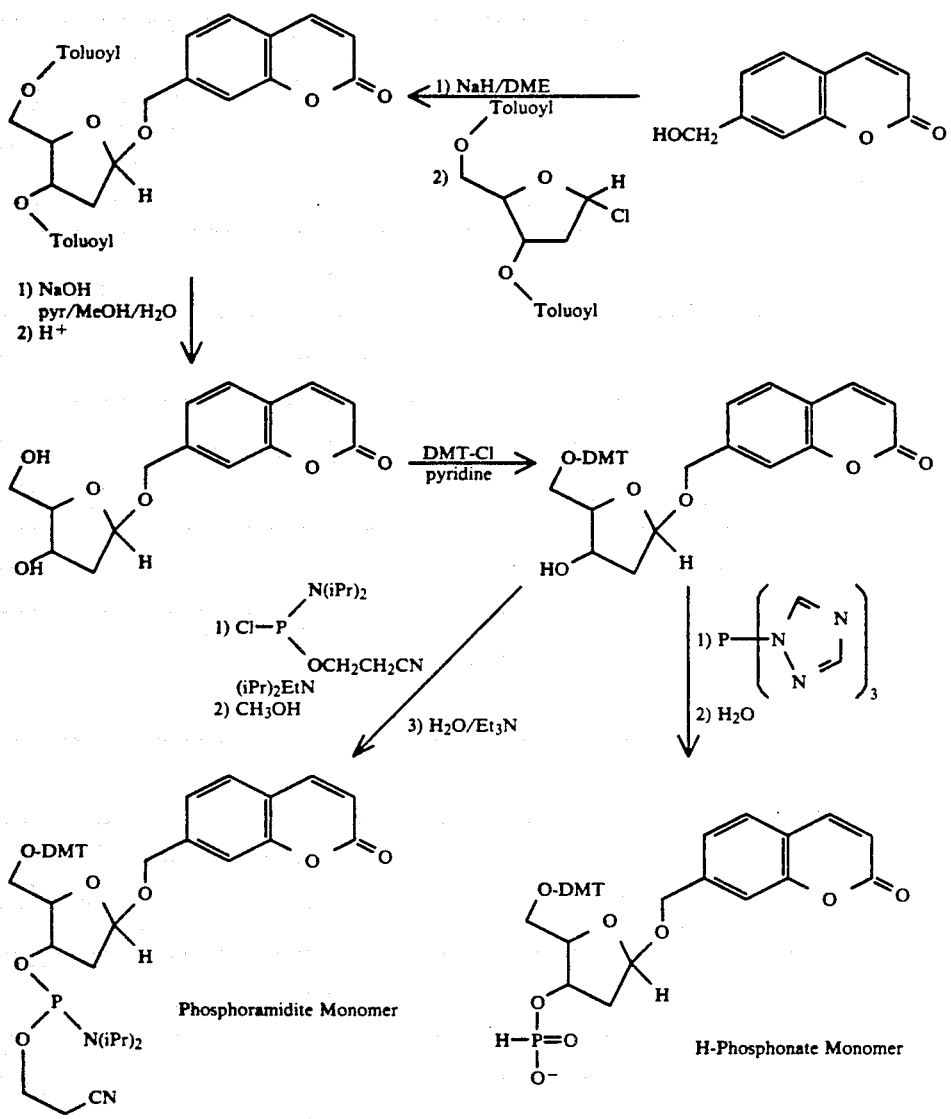

Numerous variations on this reaction scheme can be used to prepare other molecules either by selecting other starting materials or by modifying the techniques used to convert functional groups in the scheme shown above. For example, the 7-bromomethyl group provides an easily alkylated group that can be used as a precursor of more complex linking groups. Commercially available coumarins that can be used as precursors of molecules with an oxygen or other hetero atom directly attached to the aromatic coumarin ring include 7-hydroxy-3-methylcoumarin. A derivative of this molecule in which the 7-hydroxy group has been converted to a chlorocarbonylmethylene group is also available. Other useful commercially available compounds include 6-methylcoumarin, 7-methylcoumarin, 7-hydroxycoumarin, 7-hydroxy-4-methylcoumarin, 7-amino-4-methylcoumarin, 7-amino-4-trifluoromethylcoumarin, 7-carboxymethyl-4-methylcoumarin, and 7-methoxycoumarin, 4'-hydroxymethyl-4,5',8-trimethylpsoralen, 4'-aminomethyl-4,5',8-trimethylpsoralen, and angellicins. In psoralens and angellicins, the linking group comprises a portion of the furan ring; e.g., in HMT-psoralen, the linking chain can be considered to be the 4' carbon and the hydroxymethyl substitutent or the furan oxygen, the 5' and 4' carbons, and the hydroxymethyl substituent. Starting sugars include ribose and deoxyribose themselves as well as numerous other commerically available compounds that already have blocking group present at various positions. Examples include methyl-2-deoxy-3,5-di-O-(p-nitrobenzoyl)-D-ribofuranose, tri-O-benzoyl-1-acetyl-D-ribofuranose, and tetra-O-acetyl-D-ribofuranose.

As shown in the reaction scheme above, the first product obtained is typically a compound in which $R^2$ and $R^3$ are present as protected hydroxy groups. Such compounds are typically deprotected, and specific protecting or activating groups are then added in order to prepare a polynucleotide containing the nucleoside analogue of the invention. Standard techniques for the preparation of polynucleotides can be used with only minor modification, since the polymerization reaction does not involve the base analogue, only the sugar moiety. In most cases the only modification necessary is treatment of the newly synthesized, resin-oligonucleotide with 1M sodium carbonate at 50° C. for two hours prior to deblocking with hot ammonia. This treatment serves to open the coumarin ring and thereby prevent amide formation by attack of ammonia at the 2-position of the coumarin ring. Amide formation is to be avoided because it will prevent reclosure of the coumarin ring under subsequent mild acid conditions. Examples of useful techniques are set forth in M. J. Gait, ed., op. cit.

Nucleoside analogues of the invention can be incorporated into a polynucleotide either at a 3' end, a 5' end, or an interior location When a naturally occurring polynucleotide is labeled with a nucleoside analogue of the invention, the labeling typically takes place at one of the ends of the molecule or at a restriction site where manipulation of nucleotides is easier. When a nucleoside analogue of the invention is included in a synthetically prepared polynucleotide, it can easily be inserted at any location in the molecule during synthesis. The probe is otherwise chosen to be complementary to a portion of the analyte nucleotide with the exception that the probe will contain the nucleoside of the invention, which will mispair with a nucleoside in the analyte polynucleotide. The nucleotide analogue of the invention should be located in the probe such that when the probe hybridizes with its intended analyte polynucleotide, there will be a thymidine or uridine residue immediately to the 5' side of the nucleoside residue in the analyte polynucleotide that is mispaired with the nucleoside analogue of the invention. This relationship can be seen in the formula ...XpT...(5")

(5')...YpA...

showing two adjacent nucleotides in two hybridized polynucleotide chains, where T is thymidine, A is adenosine, X is any nucleotide, and Y is a nucleotide analogue of the invention, and the 5' ends of both strands are shown.

Since the nucleoside analogue of the invention does not hydrogen bond with the corresponding base in a complementary strand in a hybridization assay, some advantages are obtained by incorporating the crosslinking agent at one of the ends of the probe. For example, in a polynucleotide probe 15 bases in length, including a crosslinking agent of the invention in the center position would leave two complementary sequences 7 bases in length with some possible disruption in the center position. Since binding affinity increases exponentially with an increase in the number of sequential binding pairs, greater binding affinity is present if the crosslinking agent is present near one end of the molecule so that 12 or 13 sequential bases are complementary rather than 2 groups of seven. Locating the nucleoside analogue 1 or 2 bases from the end of the probe reduces nonspecific crosslinking and is preferred over locating the analogue at the end of the probe.

When located at or near one of the ends of the probe, the nucleoside can be either an α- or a β-anomer with little or no effect on crosslinking efficiency. When located at a central location in a probe, the nucleoside is preferably a β-anomer for increased crosslinking efficiency.

The invention now being generally described, the same will be better understood by reference to the following detailed examples which are provided for purposes of illustration and are not intended to be limiting to the invention unless as specified.

EXAMPLE 1

Preparation of 7-Bromomethylcoumarin

To 50 ml of chloroform was added 7-methylcoumarin (10 g, 62.4 mmol) and N-bromosuccinimide (11.1 g, 62.4 mmol). The suspension was then refluxed for 24 hours at which time a clear solution resulted. Reflux was continued for five days. At this point a spherical lump of crystals had formed. The reaction mixture was cooled to room temperature and was then placed in the refrigerator at 0° C. for 24 hrs. The crystals were collected by filtration and washed with a small amount of cold chloroform. After brief evacuation to remove chloroform, the crystals were dissolved in a minimum amount of boiling acetone and allowed to crystallize for several days. The crystals were collected by filtration and washed with a little cold acetone. After drying in vacuo the yield was, 7.15 g (48% of theory). The melting point was 179.5°–181.5° C.

EXAMPLE 2

Preparation of 7-Hydroxymethylcoumarin

To a 1:1 mixture of acetone and water (560 ml) was added 7-bromomethylcoumarin (7.0 g, 29.3 mmol). The resulting suspension was refluxed for 48 hrs at which time the reaction mixture became a clear solution. The solution was then cooled and neutralized with sodium bicarbonate (2.4 g, 29.3 mmol) and concentrated in vacuo to about 65 ml. A thick mass of crystals resulted. The crystals were collected by filtration to yield 5.27 g of product after drying in vacuo (100% of theory). The melting point was 116°–117° C.

EXAMPLE 3

Fusion of 7-Hydroxymethylcoumarin and 2-Deoxy-3,5-Di-O-p-Toluoyl-α-D-Ribofuranosyl Chloride (Formation of the 2'-Deoxyriboside of Hydroxymethylcoumarin)

In a 25-mm-diameter test tube with a side tubulation for applying vacuum was placed 7-hydroxymethylcoumarin (300 mg, 1.70 mmol) and 2-deoxy-3,5-di-O-p-toluoyl-α-D-ribofuranosyl chloride (600 mg, 1.54 mmol). The test tube was tightly stoppered, and about 1 mm vacuum was applied to the tube through the tubulation. The evacuated tube was then heated in an oil bath at 110° C. for 5 min. During the first 2 min of heating there was vigorous evolution of HCl gas. The reaction mixture was then cooled to room temperature, and the residue was taken up in 3 to 4 ml of a 1:1 mixture of acetone and hexane. The solution was then submitted to chromatography on a 50 mm ×150 mm silica gel column using acetone/hexane 1:1 as the eluant. The fractions containing product were identified by TLC and were pooled and concentrated to a glass. The glass was taken up in 10 ml of ethyl acetate. The ethyl acetate solution in a 50 ml Erlenmeyer flask was placed in a jar containing 20 ml of pentane. The jar was then sealed and the crystallization was allowed to proceed. Yield was 330 mg of white crystals (41% of theory); the melting point was 92°–106° C. $R_f=0.48$ in acetone/hexane 1:1. NMR showed this material to be approximately a 1:1 mixture of α and β -anomers.

EXAMPLE 4

Reaction of the Alkoxide of 7-Hydroxymethylcoumarin with 2-Deoxy-3,5-Di-O-p-Toluoyl-α-D-Ribofuranosyl Chloride (Formation of the 2'-Deoxyriboside of 7-Hydroxymethylcoumarin)

To 125 ml of 1,2-dimethoxyethane was added 7-hydroxymethylcoumarin (2.49 g, 14.15 mmol) and 50% sodium hydride in oil (747 mg, 15.57 mmol). A suspension resulted. Then 2-deoxy-3,5-di-O-p-toluoyl-α-D-ribofuranosyl chloride (5.50 g, 14.15 mmol) was added slowly and in small portions to the rapidly stirred suspension. After 5 min, 1 ml of glacial acetic acid was added to neutralize the reaction mixture. The reaction mixture was then filtered and concentrated in vacuo to an oil. The oil was then purified by silica gel chromatography using ethyl acetate/hexane (EtOAc/Hex) 1:1 as the eluant. The fractions containing product were identified by TLC and were pooled and concentrated to an oil in vacuo. The product was homogeneous by TLC. NMR showed the product to be a mixture of α- and β-anomers with an approximate ratio of 1:1. Yield: 3.77 g (50% of theory).

EXAMPLE 5

Removal of the p-Toluoyl Groups from the 3',5'-di-O-p-toluoyl-2'-deoxyriboside of 7-Hydroxymethylcoumarin The 3',5'-di-O-p-toluoyl-2'-deoxyriboside of 7-hydroxymethylcoumarin (2.6 g, 4.92 mmol) from Example 4 was dissolved in 25 ml of pyridine/methanol/water (65:30:5) and was cooled briefly in ice water. Then 25 ml of 2M NaOH in pyridine/methanol/water (65:30:5) was added with stirring in an ice bath. After 20 min the reaction was stopped by addition of 3.2 g $NH_4Cl$. The precipitate was filtered off, then concentrated in vacuo to dryness. The residue was taken up in EtOAc/acetone (9:1, 10 ml), and the solution was applied to a silica gel column 50 mm wide by 152 mm tall and eluted with EtOAc/acetone (9:1). Fractions were identified by TLC. $R_f$ of product in the elution solvent was about 0.42. The fractions containing product (mixture of α- and β-anomers) were concentrated in vacuo to yield 600 mg of product (~42% yield).

EXAMPLE 6

Preparation of the 4,4'-Dimethoxytrityl Derivative at the 5' Position of the 2'-Deoxyriboside of 7-Hydroxymethylcoumarin To 20 ml of pyridine was added 7-coumarinylmethyl-β-D-2'-deoxyriboside from Example 5 (580 mg, 1.98 mmol), 4-N,N-dimethylaminopyridine (12 mg), and triethylamine (385 µl, 2.77 mmol). To the resulting solution was added 4,4'-dimethoxytrityl chloride (812 mg, 2.40 mmol). The reaction mixture was then stirred for 3 hours. The mixture was then treated with 25 ml of water, and the resulting mixture was extracted with 2×120 ml of ethyl ether. The combined ether extracts were concentrated in vacuo, dissolved in 2.5 ml of acetone/methylene chloride (0.5:9.5), and purified by chromotagraphy on a silica gel column using the same solvent (containing 2% triethylamine). Two fractions are obtained (rf by silica gel thin layer chromatography of 0.30 and 0.40 in the same elution system). These fractions are the separated α- and β-anomers. Yield of rf 0.40 fraction: 365 mg.

EXAMPLE 7

Preparation of the H-Phosphonate of the 4,4'-Dimethoxytrityl Derivative at the 5' Position of the 2'-Deoxyriboside of 7-Hydroxymethylcoumarin Phosphorus trichloride (257.4 µl, 2.95 mmol) and N-methylmorpholine (3.24 ml, 29.5 mmol) were dissolved in 30 ml of methylene chloride. Triazole (678 mg, 9.82 mmol) was then added to the solution. After 30 min the reaction mixture was cooled to 0° C., and the DMT derivative of Example 6 (350 mg, 0.589 mmol; dried by coevaporation from $CH_3CN$) in 8 ml of dry methylene chloride was added dropwise with stirring over 20 min. After a total of 30 min from the beginning of addition, the reaction mixture was poured into 24 ml of 1M triethyammonium bicarbonate pH 8.5 and shaken in a separatory funnel. The organic phase was separated. The aqueous phase was extracted with 8 ml of methylene chloride, and the combined organic phases were dried over sodium sulfate. The dry organic phase was then concentrated to a foam, dissolved in 1.5 ml of methylene chloride/methanol/triethylamine (500:40:6), and purified by silica gel chromatography in the same solvent. Yield: ~500 mg of a glass.

EXAMPLE 8

Preparation of Oligodeoxynucleotides Containing a Nucleoside Analogue of the Invention Using the H-phosphonate method of Froehler et al. (Nucleic Acids Research (1986) 14: 5399), the following oligonucleotide was assembled:

5'—CAGCCTTXA—3'.

In this formula, X is (7-coumarinyl)methyl-β-D-2'-deoxyriboside, and A, C, G, and T have their normal meanings in nucleotides.

After assembly, the solid support bearing oligonucleotides (10 mg) was treated with 1M $Na_2CO_3$ (200 ml) for 2 hrs at 50° C. followed by addition of concentrated ammonia 2 ml and heating at 55° C. for 18 hrs. Then the oligonucleotides were purified by polyacrylamide gel electrophoresis.

The oligonucleotide was shown to be effective in specifically hybridizing and crosslinking (after photoactivation) with a target polynucleotide.

EXAMPLE 9

Preparation of 3'-O-(N-diisopropylamino)phosphoramidite Derivative of the 4,4'-Dimethoxytrityl Derivative at the 5' Position of the 2'-Deoxyriboside of 7-Hydroxymethylcoumarin Dry DMT derivative from the procedure of Example 6 (827 µg, 1.39 mmol) is treated with diisopropylethylamine (1.21 ml, 5.56 mmol) and dichloromethane (3 ml). The suspension is stirred until it becomes a clear solution. Then chloro-N,N-diisopropylaminomethoxyphosphine (400 µl, 2.09 mmol) is added. The reaction mixture is stirred for fifteen minutes, after which the reaction is stopped by addition of anhydrous methanol (20 µl ). The reaction mixture is then diluted with ethyl acetate (30 ml) and triethylamine (1.5 ml), extracted with 10% aqueous sodium carbonate (2×20 ml), and then with saturated aqueous sodium chloride (2×20 ml). The organic phase is then concentrated in vacuo.

The product is purified by chromatography on silica gel using ethyl acetate/dichloromethane/triethylamine (45:45:10) as the developing solvent. The fractions containing product are concentrated in vacuo to give a white powder. Yield is approximately 1 gram. To make cyanoethylphosphoramidites instead of methylphosphoramidites, substitute chloro-N,N-diisopropylaminocyanoethoxyphosphine (479 μl, 2.09 mmol) for chloro-N,N-diisopropylaminomethoxyphosphine.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A photoactivatable compound wherein a coumarin moiety is linked by a linking group X to a sugar moiety, said compound having the formula

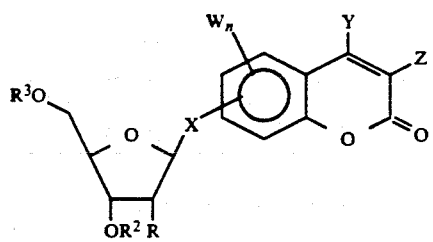

wherein
n is 0, 1, 2, or 3;
each W independently represents a halogen, nitro, cyano, cabonyl, carboxyl, hydroxy, amido or amino group; an unsubstituted hydrocarbyl group of less than 15 atoms; or a hydrocarbyl group of less than 15 atoms and being substituted with at least one of said groups;
Y and Z independently represent H or lower alkyl;
X is an organic linking group of 1 to 5 carbon atoms; 0 to 4 hetero atoms selected from the group consisting of O, S, and N; and 0 to 2m halogen atoms, where m is the number of carbon atoms in X, and wherein a single linking chain of 1 to 4 atoms in X joins the phenyl ring of said coumarin moiety to the 1-position of said sugar moiety;
R is H or $-OR^1$;
$R^1$, $R^2$, and $R^3$ independently represent H or a hydroxyl-protecting or hydroxyl-coupling organic group capable of coupling or protecting a hydroxyl group during polynucleotide synthesis or $R^2$ or $R^3$ represent a nucleotide of a polynucleotide linked to said compound by a 3'-5' phosphodiester linkage.

2. The compound of claim 1, wherein said linking group is covalently attached to the 7 position of the coumarin moiety.

3. The compound of claim 1, wherein R is H or —OH and $R^2$ and $R^3$ independently represent H or a nucleotide or a polynucleotide linked to said compound by a 3'-5' phosphodiester linkage.

4. The compound of claim 1, wherein X is $X^2$, $OX^2$, $SX^2$ or $NHX^2$, wherein $X^2$ is a $C_1$–$C_5$ hydrocarbyl group or a $C_1$–$C_5$ hydrocarbyloxy group substituted with 0 to 2 carbonyl oxygens, with the proviso that when said O, S, or NH is present as part of X, a carbon atom of $X^2$ attaches to said O, S, or N and said O, S, or NH is attached to the 1' portion of the furanose ring of said formula.

5. The compound of claim 4, wherein X is $X^2$ or $OX^2$ wherein $X^2$ is as defined in claim 11.

6. The compound of claim 1, wherein X is

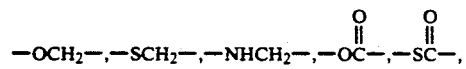
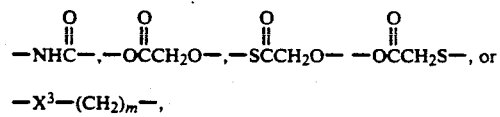

where m is an integer from 2 to 4 and $X^3$ is —NH—, —O—, or —S—.

7. The compound of claim 1 wherein $R^1$ is H.

8. The compound of claim 1, wherein $R^1$ is 4-methoxytetrahydropyran-4-yl.

9. The compound of claim 1 wherein $R^2$ is H; benzoyl; benzoyl substituted with $C_1$–$C_4$ alkyl, $C_1$–$C_4$ alkoxyl, cyano, nitro, or halogen; trityl; or trityl substituted with $C_1$–$C_4$ alkyl or alkoxyl, cyano, nitro, or halogen.

10. The compound of claim 1 wherein $R^3$ is H; benzoyl; benzoyl substituted with $C_1$–$C_4$ alkyl, $C_1$–$C_4$ alkoxyl, cyano, nitro, or halogen; trityl; or trityl substituted with $C_1$–$C_4$ alkyl or alkoxyl, cyano, nitro, or halogen.

* * * * *